United States Patent
Meglan et al.

(10) Patent No.: US 11,986,261 B2
(45) Date of Patent: May 21, 2024

(54) SYSTEMS AND METHODS FOR SURGICAL ROBOTIC CART PLACEMENT

(71) Applicant: Covidien LP, Mansfield, MA (US)

(72) Inventors: Dwight Meglan, Westwood, MA (US); Eric Meade, Pocasset, MA (US); Samir Zahine, Billerica, MA (US); Renen Bassik, Lexington, MA (US); Mathew Livianu, Malden, MA (US)

(73) Assignee: COVIDIEN LP, Mansfield, MA (US)

( * ) Notice: Subject to any disclaimer, the term of this patent is extended or adjusted under 35 U.S.C. 154(b) by 854 days.

(21) Appl. No.: 17/047,867

(22) PCT Filed: Apr. 1, 2019

(86) PCT No.: PCT/US2019/025108
§ 371 (c)(1),
(2) Date: Oct. 15, 2020

(87) PCT Pub. No.: WO2019/204013
PCT Pub. Date: Oct. 24, 2019

(65) Prior Publication Data
US 2021/0153958 A1     May 27, 2021

Related U.S. Application Data

(60) Provisional application No. 62/660,476, filed on Apr. 20, 2018.

(51) Int. Cl.
*G06F 7/00* (2006.01)
*A61B 34/20* (2016.01)
(Continued)

(52) U.S. Cl.
CPC .............. *A61B 34/32* (2016.02); *A61B 34/20* (2016.02); *A61B 34/35* (2016.02); *A61B 50/13* (2016.02);
(Continued)

(58) Field of Classification Search
CPC ......... A61B 34/32; A61B 34/20; A61B 34/35; A61B 50/13; A61B 90/36;
(Continued)

(56) References Cited

U.S. PATENT DOCUMENTS

| 6,132,368 A | 10/2000 | Cooper |
| 6,154,139 A | 11/2000 | Heller |

(Continued)

FOREIGN PATENT DOCUMENTS

| CN | 107072723 A | 8/2017 |
| CN | 107072726 A | 8/2017 |

(Continued)

OTHER PUBLICATIONS

International Search Report dated Jul. 18, 2019 and Written Opinion completed Jul. 18, 2019 corresponding to counterpart Int'l Patent Application PCT/US2019/025108.

(Continued)

*Primary Examiner* — Yolanda R Cumbess
(74) *Attorney, Agent, or Firm* — Carter, DeLuca & Farrell LLP (57) ABSTRACT

A method of placing a surgical robotic cart assembly includes, determining a first position of a first surgical robotic cart assembly relative to a surgical table, calculating a path for the first surgical robotic cart assembly towards a second position of the first surgical robotic cart assembly relative to the surgical table, wherein in the second position, the first surgical robotic cart assembly is spaced-apart a first safe distance from the surgical table, moving the first surgical robotic cart assembly autonomously towards the second position thereof, and detecting a potential collision along the path of the first surgical robotic cart assembly as the first surgical robotic cart assembly moves towards the second position thereof.

18 Claims, 8 Drawing Sheets

(51) Int. Cl.
*A61B 34/32* (2016.01)
*A61B 34/35* (2016.01)
*A61B 50/13* (2016.01)
*A61B 90/00* (2016.01)
*B25J 5/00* (2006.01)
*B25J 9/16* (2006.01)

(52) U.S. Cl.
CPC ............ *A61B 90/36* (2016.02); *B25J 5/007* (2013.01); *B25J 9/162* (2013.01); *A61B 2034/2055* (2016.02); *A61B 2034/2063* (2016.02); *A61B 2090/365* (2016.02); *A61B 2090/3937* (2016.02)

(58) Field of Classification Search
CPC .... A61B 2034/2055; A61B 2034/2063; A61B 2090/365; A61B 2090/3937; A61B 34/37; B25J 5/007; B25J 9/162; G05D 1/0231; G05D 1/0274; G05D 1/0282; G05D 2201/0206
USPC .......................................... 700/213–214, 228
See application file for complete search history.

(56) References Cited

U.S. PATENT DOCUMENTS

| | | |
|---|---|---|
| 6,205,396 B1 | 3/2001 | Teicher et al. |
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,374,155 B1 | 4/2002 | Wallach et al. |
| 6,394,998 B1 | 5/2002 | Wallace et al. |
| 6,424,885 B1 | 7/2002 | Niemeyer et al. |
| 6,438,456 B1 | 8/2002 | Feddema et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,507,771 B2 | 1/2003 | Payton et al. |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,845,297 B2 | 1/2005 | Allard |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,941,191 B2 | 9/2005 | Jaeger |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,667,606 B2 | 2/2010 | Packert et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,112,172 B2 | 2/2012 | Chen et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,205,396 B2 | 6/2012 | Atiyeh, Sr. et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,244,403 B2 | 8/2012 | Lin et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |

(56) References Cited

U.S. PATENT DOCUMENTS

| | | |
|---|---|---|
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,446,288 B2 | 5/2013 | Mizushima et al. |
| 8,452,447 B2 | 5/2013 | Nixon |
| 8,454,585 B2 | 6/2013 | Whitman |
| 8,478,442 B2 | 7/2013 | Casey et al. |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,956 B1 | 1/2014 | Chiappetta et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,798,840 B2 | 8/2014 | Fong et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,983,662 B2 | 3/2015 | Moore |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,048 B2 | 3/2016 | Kostrzewski et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,902,061 B1 * | 2/2018 | Kuffner .................. B25J 9/163 |
| 9,918,800 B2 | 3/2018 | Itkowitz et al. |
| 9,943,375 B2 | 4/2018 | Blumenkranz et al. |
| 9,943,964 B2 | 4/2018 | Hares |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |

(56) References Cited

U.S. PATENT DOCUMENTS

| | | |
|---|---|---|
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,944 B2 | 3/2020 | Lattimore |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stem et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2006/0195226 A1 | 8/2006 | Matsukawa et al. |
| 2007/0112461 A1* | 5/2007 | Zini ............... G05D 1/0242 |
| | | 700/245 |
| 2007/0118248 A1 | 5/2007 | Lee et al. |
| 2008/0275630 A1 | 11/2008 | Regienczuk |
| 2008/0287924 A1 | 11/2008 | Mangiardi |
| 2009/0117312 A1 | 5/2009 | Hanelt et al. |
| 2012/0101508 A1 | 4/2012 | Wook Choi et al. |
| 2014/0316570 A1 | 10/2014 | Sun et al. |
| 2015/0257837 A1 | 9/2015 | Itkowitz et al. |
| 2016/0346930 A1 | 12/2016 | Hares |
| 2017/0071693 A1 | 3/2017 | Taylor et al. |
| 2017/0123421 A1 | 5/2017 | Kentley et al. |
| 2017/0251990 A1 | 9/2017 | Kheradpir et al. |
| 2018/0042682 A1 | 2/2018 | Iceman et al. |
| 2018/0344421 A1* | 12/2018 | Cagle ............... B25J 9/0009 |
| 2019/0041854 A1* | 2/2019 | Millhouse ............... H04W 4/02 |
| 2019/0069962 A1 | 3/2019 | Tabandeh et al. |

FOREIGN PATENT DOCUMENTS

| | | | |
|---|---|---|---|
| CN | 107787266 A | 3/2018 | |
| EP | 3212109 A1 | 9/2017 | |
| KR | 101613376 B1 | 4/2016 | |
| WO | 2016193686 A1 | 12/2016 | |
| WO | 2017147596 A1 | 8/2017 | |
| WO | WO-2017147596 A1 * | 8/2017 | ............ A61B 34/00 |
| WO | 2017220822 A1 | 12/2017 | |
| WO | 2019203999 A1 | 10/2019 | |

OTHER PUBLICATIONS

Indian Office Action dated Jan. 17, 2022 issued in corresponding IN Appln No. 202017040919.

Partial Supplementary European Search Report dated Dec. 15, 2021 issued in corresponding EP Appln. No. 19788524.7.

Japanese Office Action dated Sep. 7, 2021 corresponding to counterpart Patent Application JP 2020-555060.

Japanese Notice of Allowance dated May 2, 2022 issued in corresponding JP Appln. No. 2020-555060.

Extended European Search Report dated Mar. 22, 2022, issued in corresponding EP Appln. No. 19788524.7.

Office Action issued in corresponding Chinese application CN 201980025810.3 dated Feb. 12, 2023, together with English language translation (16 pages).

European Examination Report issued in corresponding application EP 19788524.7 dated Oct. 19, 2023.

* cited by examiner

SYSTEMS AND METHODS FOR SURGICAL ROBOTIC CART PLACEMENT

CROSS-REFERENCE TO RELATED APPLICATIONS

This application is a U.S. National Stage Application filed under 35 U.S.C. § 371(a) of International Patent Application Serial No. PCT/US2019/025108, filed Apr. 1, 2019, which claims the benefit of and priority to U.S. Provisional Patent Application Ser. No. 62/660,476, filed Apr. 20, 2018, the entire disclosure of each of which are incorporated by reference herein.

BACKGROUND

Technical Field

The present disclosure relates to movable surgical robotic systems and, more particularly, to systems and methods facilitating placement of one or more surgical robotic cart assemblies relative to a surgical table.

Background of Related Art

Surgical robotic systems are used in minimally invasive medical procedures because of their increased accuracy and expediency. In surgical robotic systems, a robot arm supports a surgical instrument having an end effector mounted thereto by a wrist assembly. In operation, the robot arm inserts the surgical instrument into or holds a surgical instrument in a small incision via a surgical portal or a natural orifice of a patient to position the end effector at a work site within a patient's body.

Most of the surgical robotic systems on the market are heavy and stationary requiring a motor driven pallet jack to be relocated. In some of the more modern surgical robotic systems, the robot arm is supported on a movable surgical robotic cart having a base portion with a set of casters. This is beneficial because the surgical robotic systems can be moved between various rooms and between various positions relative to the surgical table as needed, without a pallet jack.

However, minimally invasive medical procedures require a high degree of accuracy, precision, and speed, and, therefore, movable surgical robotic systems used for minimally invasive medical procedures need to be precisely placed relative to the surgical table to achieve optimal positioning for specific surgical procedures.

Accordingly, there is a need to precisely locate and position a surgical robotic cart relative to the surgical table, and to do so with a high degree of accuracy, precision, and movability.

SUMMARY

Provided in accordance with aspects of the present disclosure is a method of placing a surgical robotic cart assembly. The method includes, determining a first position of a first surgical robotic cart assembly relative to a surgical table, calculating a path for the first surgical robotic cart assembly towards a second position of the first surgical robotic cart assembly relative to the surgical table, wherein in the second position, the first surgical robotic cart assembly is spaced-apart a first safe distance from the surgical table, moving the first surgical robotic cart assembly autonomously towards the second position thereof, and detecting a potential collision along the path of the first surgical robotic cart assembly as the first surgical robotic cart assembly moves towards the second position thereof.

In one aspect of the present disclosure, the method further includes determining a first position of a second surgical robotic cart assembly relative to the first surgical robotic cart assembly and the surgical table, calculating a path for the second surgical robotic cart assembly towards a second position of the second surgical robotic cart assembly relative to the first surgical robotic cart assembly and the surgical table, wherein in the second position, the second surgical robotic cart assembly is spaced-apart a second safe distance from the first surgical robotic cart assembly and a third safe distance from the surgical table, moving the second surgical robotic cart assembly autonomously towards the second position thereof, and detecting a potential collision along the path of the second surgical robotic cart assembly as the second surgical robotic cart assembly moves towards the second position thereof.

In another aspect of the present disclosure, the method may include obtaining a first sensor data from a visual sensor to determine the first position of the first surgical robotic cart assembly and to determine the first position of the second surgical robotic cart assembly.

In yet another aspect of the present disclosure, the method may include obtaining a second sensor data from a floor sensor to determine the first position of the first surgical robotic cart assembly and to determine the first position of the first surgical robotic cart assembly.

In still another aspect of the present disclosure, the method may include obtaining a third sensor data from the first surgical robotic cart assembly to determine the first position of the second surgical robotic cart assembly.

In aspects of the present disclosure, the method may include obtaining a fourth sensor data from the surgical table to determine the first position of the first surgical robotic cart assembly.

In one aspect of the present disclosure, the method may include updating an environmental map to incorporate the first position of the first surgical robotic cart assembly and the first position of the second surgical robotic cart assembly.

In another aspect of the present disclosure, the method may include determining a third position for the second surgical robotic cart assembly upon detecting the potential collision between the second surgical robotic cart assembly and the first surgical robotic cart assembly.

In yet another aspect of the present disclosure, the method may include determining the requirement for troubleshooting of the second surgical robotic cart assembly upon detecting the potential collision between the second surgical robotic cart assembly and the first surgical robotic cart assembly.

In still another aspect of the present disclosure, the method may include moving the first surgical robotic cart assembly and the second surgical robotic cart assembly simultaneously towards the respective second positions thereof.

Provided in accordance with another aspect of the present disclosure is a method of positioning a plurality of surgical robotic cart assemblies within an operating room. The method includes, obtaining a first sensor data from an operating room sensor, determining a first position of a first surgical robotic cart assembly and determining a first position of a second surgical robotic cart assembly, the first surgical robotic cart assembly including a first base portion having a first sensor and a first transmitter, and the second surgical robotic cart assembly including a second base portion having a second sensor and a second transmitter, calculating a first path for the first surgical robotic cart assembly towards a second position of the first surgical robotic cart assembly and calculating a second path for the second surgical robotic cart assembly towards a second position of the second surgical robotic cart assembly, moving the first surgical robotic cart assembly and the second surgical robotic cart assembly autonomously towards the second positions, respectively, thereof, detecting a potential collision along the first path and the second path as the first surgical robotic cart assembly moves towards the second position thereof and as the second surgical robotic cart assembly moves towards the second position thereof, and updating an environmental map with the second position of the first surgical robotic cart assembly and with the second position of the second surgical robotic cart assembly upon moving the first and second surgical robotic cart assemblies to the second positions, respectively, thereof.

In one aspect of the present disclosure, the method may include determining the first position of the first surgical robotic cart assembly and determining the first position of the second surgical robotic cart assembly from the first sensor data obtained from the operating room sensor.

In another aspect of the present disclosure, the method may include obtaining a second sensor data from the first sensor of the first surgical robotic cart assembly to determine the first position of the second surgical robotic cart assembly.

In yet another aspect of the present disclosure, the method may include obtaining a third sensor data from the second sensor of the second surgical robotic cart assembly to determine the first position of the first surgical robotic cart assembly.

In still another aspect of the present disclosure, the method may include calculating the second position of the first surgical robotic cart assembly and calculating the second position of the second surgical robotic cart assembly to maintain a first safe distance between the first and second surgical robotic cart assemblies and to maintain a second safe distance between the first and second surgical robotic cart assemblies and a surgical table.

In one aspect of the present disclosure, the method may include moving the second surgical robotic cart assembly autonomously to a third position thereof when a distance between the first and second surgical robotic cart assemblies is less than the first safe distance.

In another aspect of the present disclosure, the method may include updating the environmental map to register the third position of the second surgical robotic cart assembly as a current position of the second surgical robotic cart assembly when the second surgical robotic cart assembly is moved to the third position thereof.

Provided in accordance with yet another aspect of the present disclosure is a surgical robotic cart assembly. The surgical robotic cart assembly includes a robotic arm and a base portion configured to operatively support the robotic arm thereon. The base portion includes a visual guidance system having a projector mounted on the base portion, a display mounted on the base portion, and a plurality of lights mounted on the base portion and spaced apart thereon. The projector is configured to project a pattern corresponding to a movement direction towards a target location. The display is configured to represent a visual indication corresponding to the movement direction towards the target location. At least one of the plurality of lights is configured to selectively illuminate corresponding to the movement direction towards the target location.

In one aspect of the present disclosure, the pattern projected by the projector may be configured to change as the base portion is moved along the pattern towards the target location.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of exemplary embodiment(s) given below, serve to explain the principles of the disclosure, wherein.

DETAILED DESCRIPTION

The present disclosure provides systems and methods facilitating automated and manual means for locating and moving one or more surgical robotic cart assemblies towards a target location to optimally position one or more robotic arm(s) relative to a surgical table. Embodiments of the present disclosure are described in detail with reference to the drawings, in which like reference numerals designate identical or corresponding elements in each of the several views.

Figure 1:
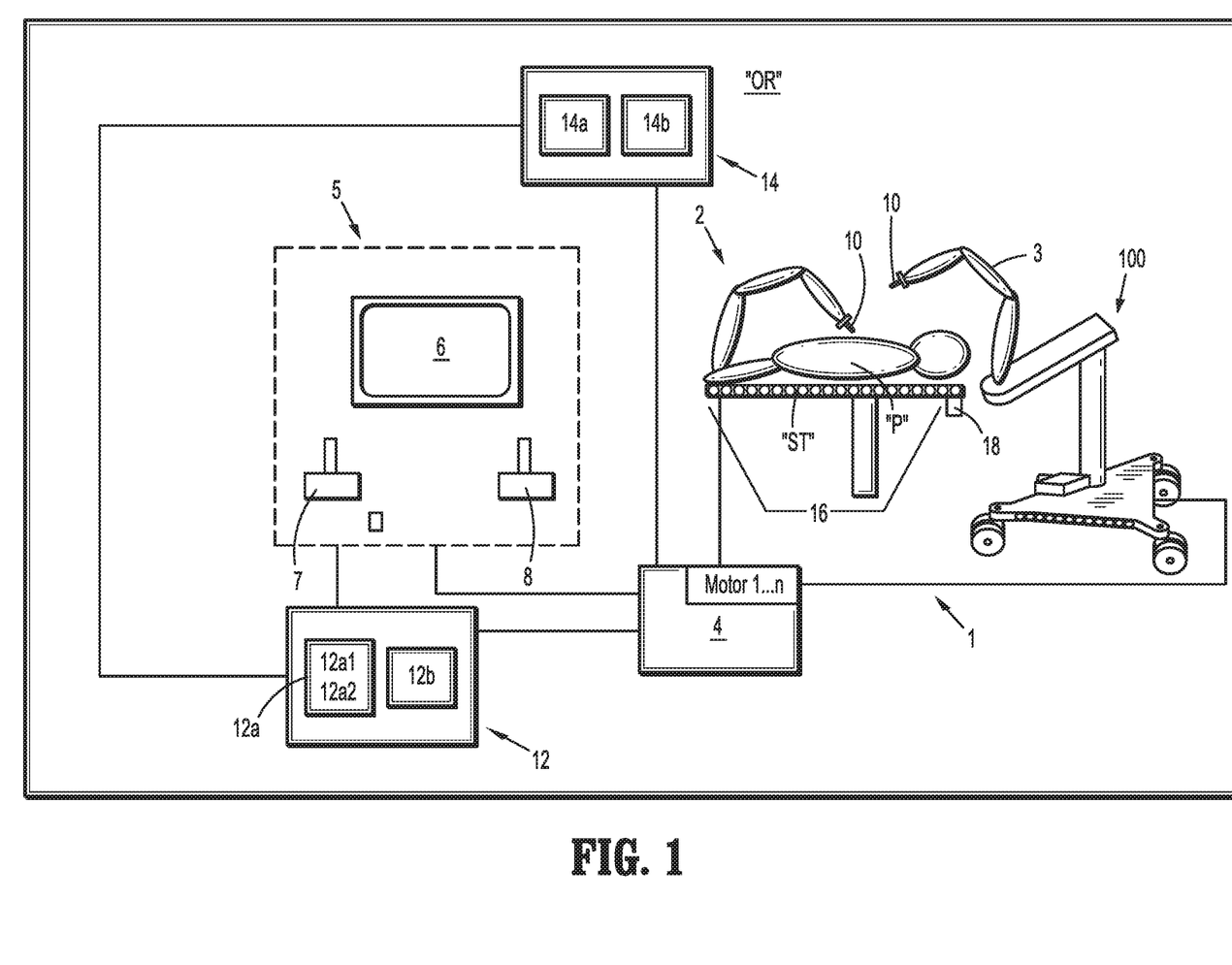
FIG. 1 is a schematic illustration of a robotic surgical system including a robotic surgical assembly in accordance with the present disclosure.

Referring initially to FIG. 1, a surgical system, such as, for example, a robotic surgical system 1 is shown. In embodiments, robotic surgical system 1 is configured for use in an operating room "OR," and specifically configured for use on a patient "P" lying on a surgical table "ST" to be treated in a minimally invasive manner by means detailed below. Robotic surgical system 1 generally includes a plurality of robotic arms 2, 3; a control device 4; and an operating console 5 coupled with control device 4.

In embodiments, surgical table "ST" includes one or more sensor(s) 16 and a transmitter 18 disposed about the periphery thereof. Sensor(s) 16 may be configured to receive, for example, radio frequency (RF) signals (e.g., ultra wide band RF signals); ultrasound waves; and infrared (IR) signals, and transmitter 18 may be configured to emit the same.

Robotic arms, such as for example, robotic arm 2 may be coupled to the surgical table "ST." Alternatively, robotic arms, such as for example, robotic arm 3, may be supported on a surgical robotic cart assembly 100.

Operating console 5 includes a display device 6, which is set up in particular to display three-dimensional images; and manual input devices 7, 8, by means of which a person (not shown), e.g., a surgeon, is able to telemanipulate robotic arms 2, 3 in a first operating mode, as known in principle to a person skilled in the art. Each of the robotic arms 2, 3 may be composed of a plurality of members, which are connected through joints, and may include a surgical instrument, such as, for example, an electromechanical instrument 10 removably attached thereto for treating patient "P" in a minimally invasive manner.

Robotic arms 2, 3 may be driven by electric drives (not shown) that are connected to control device 4. Control device 4 (e.g., a computer) is set up to activate the drives, in particular by means of a computer program, in such a way that robotic arms 2, 3 and thus electromechanical instrument 10 (including the electromechanical end effector (not shown)) execute a desired movement according to a movement defined by means of manual input devices 7, 8. Control device 4 may also be set up in such a way that it regulates the movement of robotic arms 2, 3 and/or of the drives. In embodiments, surgical robotic cart assembly 100 may be controlled via manual input devices 7, 8. Additionally/alternatively, control device 4 may be configured to regulate the movement of surgical robotic cart assembly 100.

Figure 4:
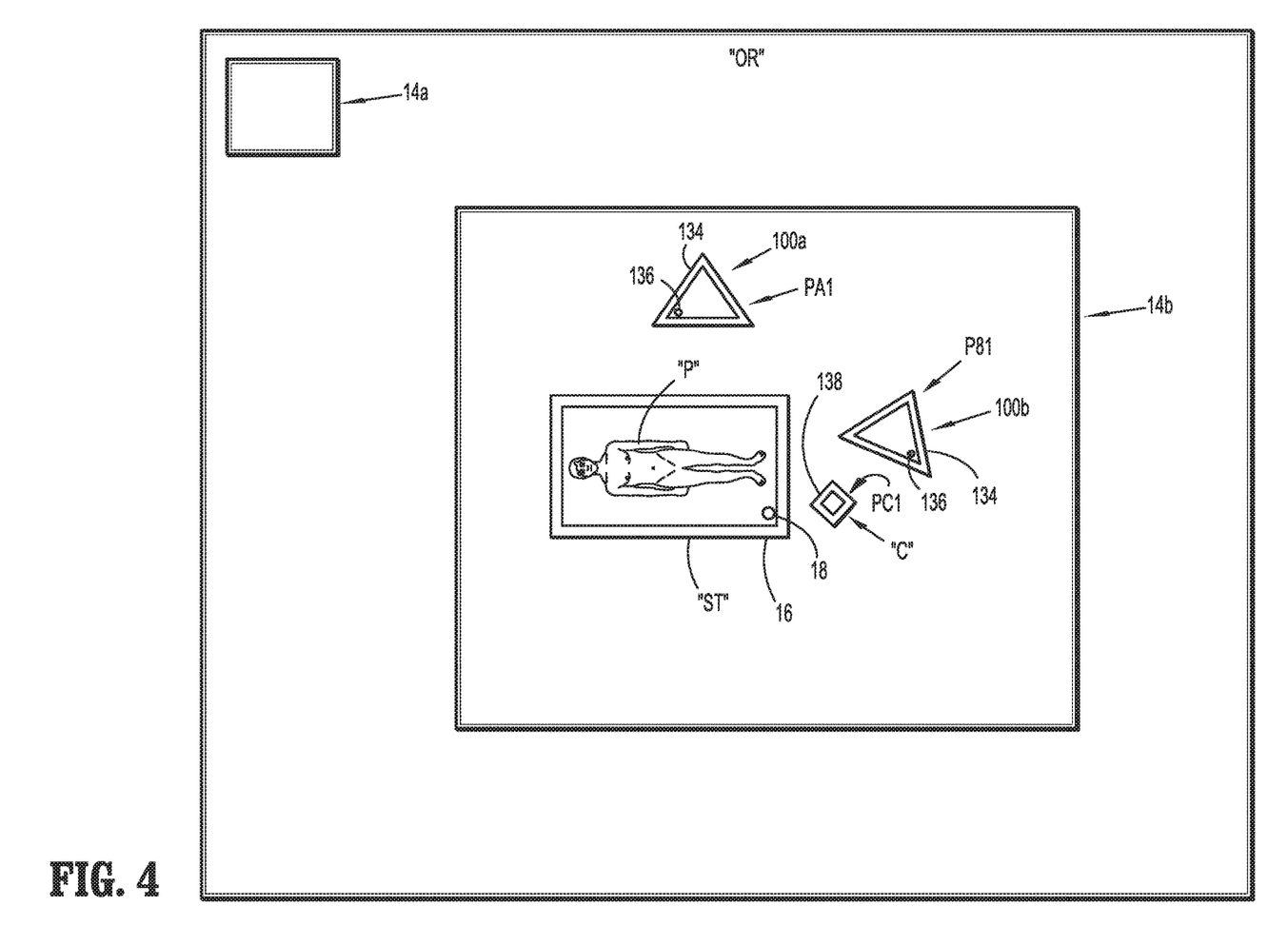
FIG. 4 is a top, plan view of an operating room of the robotic surgical system of FIG. 1, illustrating a plurality of surgical robotic cart assemblies in a first position.
Figure 5:
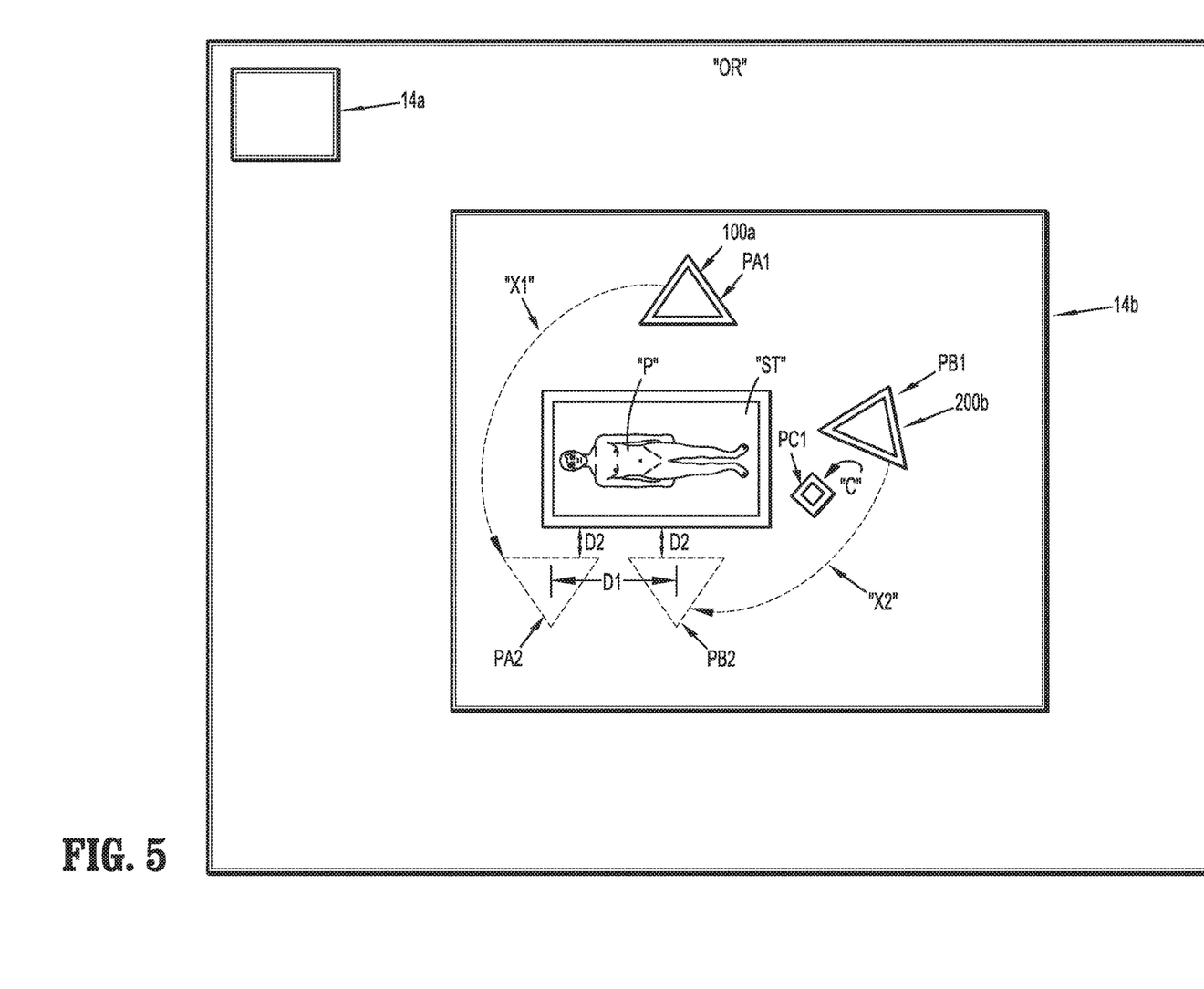
FIG. 5 is a top, plan view of the operating room of FIG. 4, illustrating the plurality of surgical robotic cart assemblies in a second position.
Figure 6:
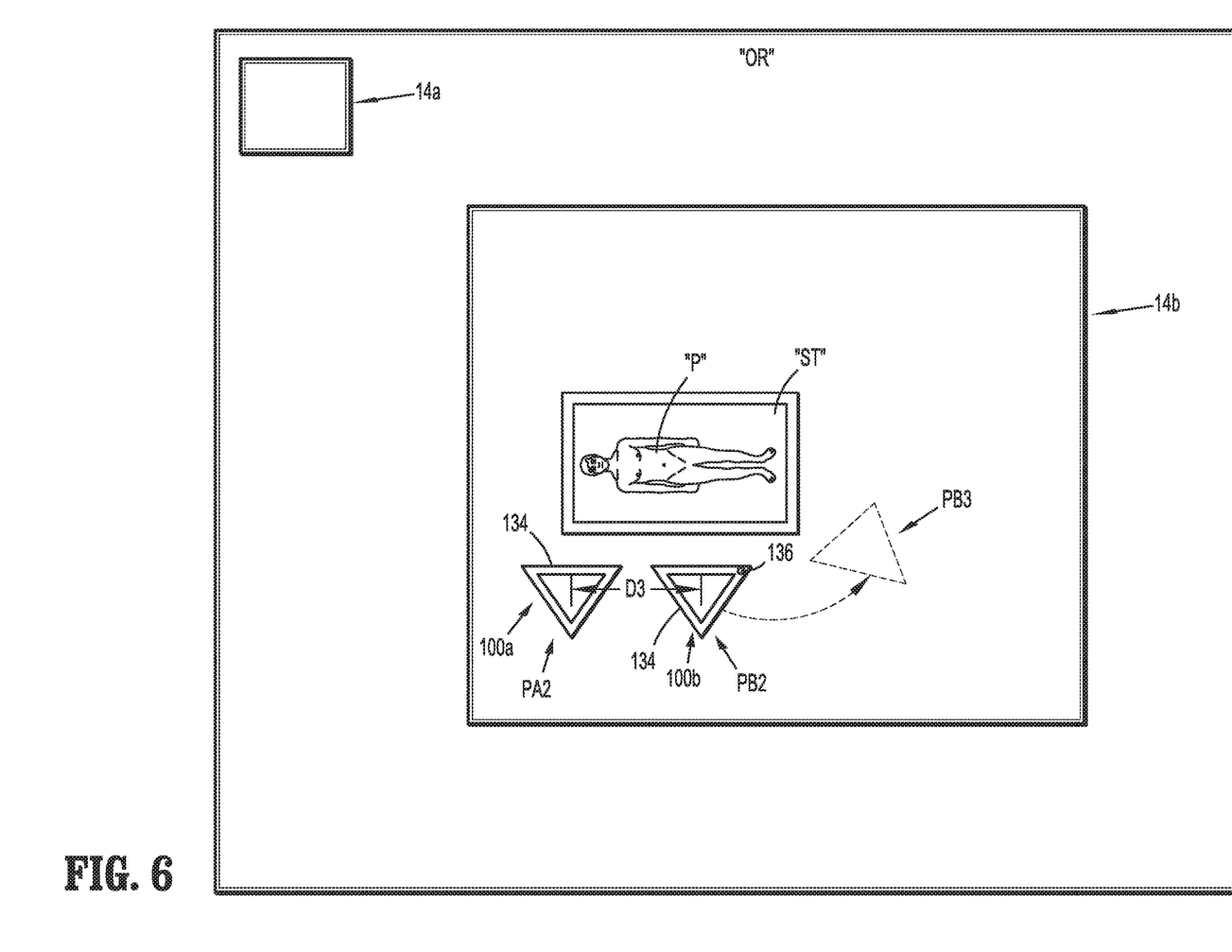
FIG. 6 is a top, plan view of the operating room of FIG. 4, illustrating the plurality of surgical robotic cart assemblies in a third position.

Robotic surgical system 1 may also include more than two robotic arms 2, 3, the additional robotic arms likewise being connected to control device 4 and being telemanipulatable by means of operating console 5. A surgical instrument, for example, electromechanical instrument 10 (including the electromechanical end effector), may also be attached to the additional robotic arm. Robotic surgical system 1 may also include a plurality of surgical robotic cart assemblies 100 for supporting robotic arms 3, such as, for example, a first surgical robotic cart assembly 100a and a second surgical robotic cart assembly 100b, as shown in FIGS. 4-6. First and second surgical robotic cart assemblies 100a, 100b are likewise configured to be connected to control device 4 and/or manual input devices 7, 8.

In embodiments, robotic surgical system 1 further includes a database 12 in communication with one or more operating room sensors 14. Database 12 is provided to store one or more environmental maps 12a representing the locations of entities (e.g., surgical table "ST" and first and second surgical robotic cart assemblies 100a, 100b) disposed within operating room "OR." Environmental maps 12a may be generated from pre-programed input and/or generated from data collected from operating room sensors 14 and/or data gathered from surgical table "ST" and first and second surgical robotic cart assemblies 100a, 100b, as will be detailed below. Environmental maps 12a include a static map portion 12a1 and a dynamic map portion 12a2. Static map portion 12a1 represents dimensions or boundaries of operating room "OR" and the locations of any landmarks such as, for example, surgical table "ST." Dynamic map portion 12a2 represents a current working environment generated by iteratively incorporating data informing of the current positions of movable entities such as, for example, first and second surgical robotic cart assemblies 100a, 100b.

Database 12 may also include patient data 12b such as, for example, pre-operative data and/or anatomical atlases assigned to patient "P." Database 12 may also be coupled with operating console 5 such that environmental maps 12a and/or patient data 12b may be displayed on display device 6.

Operating room sensors 14 may include a visual sensor 14a mounted to the ceiling of operating room "OR" and a floor sensor 14b disposed about surgical table "ST." Visual sensor 14a may include one or more cameras, video cameras, and/or imagers configured to detect the three-dimensional geometry of a base portion 130 of surgical robotic cart assembly 100 (FIG. 2) and surgical table "ST." In embodiments, visual sensor 14a may be configured to identify and track a unique marker "M" such as, for example, an indicia and/or geometric marking disposed on base portion 130 of surgical robotic cart assembly 100. Floor sensor 14b may be incorporated within a sensorized floor covering and configured to detect a pose or orientation of base portion 130 of surgical robotic cart assembly 100. Database 12 and operating room sensors 14 are coupled with control device 4 such that control device 4 may incorporate the information from environmental maps 12a, patient data 12b, and operating room sensors 14 in regulating the movement of surgical cart robotic assembly 100.

As shown in FIG. 1, the various components of robotic surgical system 1 detailed above may be coupled to one another via a wired and/or wireless means to send and receive data therebetween.

For a detailed discussion of the construction and operation of a robotic surgical system, reference may be made to U.S. Pat. No. 8,828,023, filed on Nov. 3, 2011, entitled "Medical Workstation," the entire content of which is incorporated herein by reference.

Figure 2:
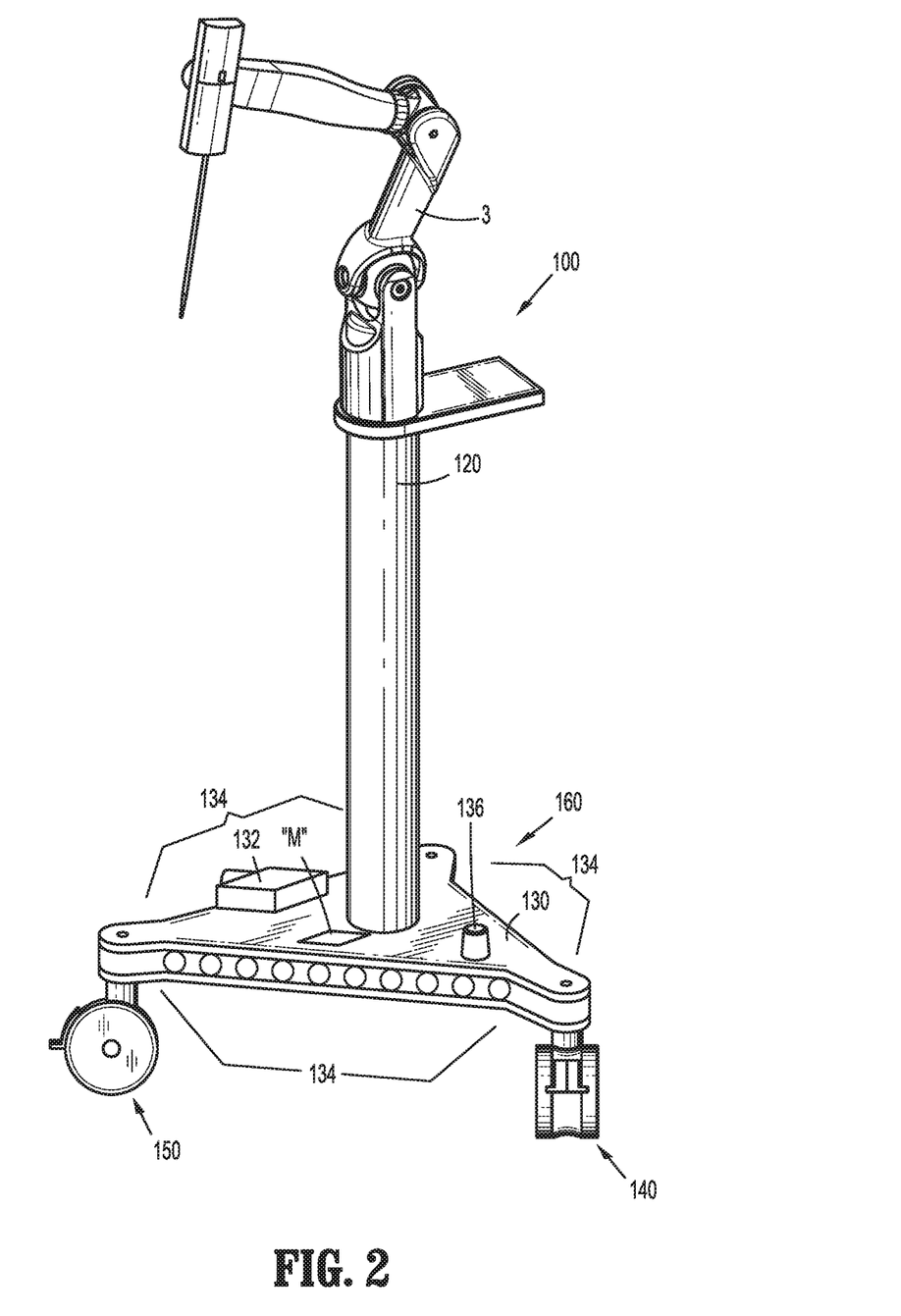
FIG. 2 is a perspective view of a surgical robotic cart assembly of the robotic surgical system of FIG. 1, illustrating a robotic arm supported on a base portion in accordance with an embodiment the present disclosure.

With reference to FIG. 2, one exemplary embodiment of surgical robotic cart assembly 100 configured for use in accordance with the present disclosure is generally identified, although it is also envisioned that the aspects and features of the present disclosure be similarly incorporated into any suitable surgical robotic cart assembly. Surgical robotic cart assembly 100 generally includes robotic arm 3, a vertical column 120, and a base portion 130. Base portion 130 includes a plurality of casters 140, 150, and 160 coupled thereto. Each of the casters 140, 150, and 160 is configured to swivel about a respective pivot axis, and configured to allow surgical robotic cart assembly 100 to move, or to inhibit movement of surgical robotic cart assembly 100.

For a detailed discussion of the construction and operation of a surgical robotic cart assembly, reference may be made to U.S. patent application Ser. No. 15/765,544 filed on Apr. 3, 2018, now U.S. Pat. No. 10,595,944, entitled "SURGICAL ROBOTIC CART WITH SELECTIVE WHEEL ALIGNMENT," and/or International Patent Application Serial No. PCT/US2019/024509 filed on Mar. 28, 2019, published as WO 2019/203999, entitled "ROBOTIC SURGICAL SYSTEMS AND ROBOTIC ARM CARTS THEREOF," the entire contents of each of which are incorporated herein by reference.

Continuing with FIG. 2, surgical robotic cart assembly 100 includes a camera 132, one or more sensor(s) 134, a transmitter 136, and a unique marker "M" disposed on base portion 130. In embodiments, sensor(s) 134 may be spaced apart and disposed along the periphery of base portion 130, such that, the relative pose or orientation of base portion 130 may be obtained by determining which of the sensor(s) 134 is first to receive a signal from a source, such as, for example, transmitter 136 of a second surgical robotic cart assembly 100b (FIG. 4) and/or transmitter 18 of surgical table "ST." Alternatively, camera 132, sensor(s) 134, transmitter 136, and unique marker "M" may be disposed about other components (e.g., vertical column 120) of surgical robotic cart assembly 100.

Similar to sensor(s) 16 of surgical table "ST," sensor(s) 134 may be configured to receive, for example, RF signals (e.g., ultra wide band RF signals); ultrasound waves; and IR signals, and similar to transmitter 18 of surgical table "ST," transmitter 136 may be configured to emit the same. As will be detailed below with reference to FIGS. 3-6, it is contemplated that sensor(s) 16 and transmitter 18 of surgical table "ST" and camera 132, sensor(s) 134, and transmitter 136 of surgical robotic cart assembly 100 are configured to cooperate to provide an accurate and robust localization of, for example, first surgical robotic cart assembly 100a relative to second surgical robotic cart assemblies 100b and surgical table "ST" disposed within operating room "OR." Further, sensor(s) 16 and transmitter 18 of surgical table "ST" and camera 132, sensor(s) 134, and transmitter 136 are configured to cooperate to provide an accurate measurement of the relative orientation of each of the plurality of surgical robotic cart assemblies 100 relative to surgical table "ST."

With reference to FIGS. 3-6, in conjunction with FIGS. 1 and 2, an exemplary method of using robotic surgical system 1 for automatically positioning first surgical robotic cart assembly 100a and second surgical robotic cart assembly 100b around surgical table "ST" such that, robotic arms 3 of first and second surgical robotic cart assemblies 100a, 100b are optimally positioned relative to each other and surgical table "ST" to complete a specified task, is described. Although only two surgical robotic cart assemblies are described, it is contemplated that any number of surgical robotic cart assemblies may be incorporated into robotic surgical system 1. The process of positioning first and second surgical robotic cart assemblies 100a, 100b around surgical table "ST" generally includes a localization phase (e.g., step S200), a path planning phase (e.g., step S208), a movement phase (e.g., step S214), and a confirmation of placement phase (e.g., step S224), as will be detailed below. It is contemplated that robotic surgical system 1 provides a safety system incorporated into the various phases detailed below, to prevent inadvertent collisions between first and second surgical robotic cart assemblies 100a, 100b and any entities located within operating room "OR." This safety system would incorporate sensors, such as for example LIDAR which generates a cloud of 3D surface points of objects, that discern the physical presence of the edges or periphery/boundary of the arms and table relative to one another. The safety system would combine this boundary information with the current movement as well as predicted future movement of the carts relative to one another and the surgical table to decide if a collision is possible and if so adjusted the path(s) of the cart(s) relative to one another and/or the surgical table. This safety system could also combine the known geometric configuration of the arms and/or surgical table along with the known pose of the same to compute potential collisions and take corrective action to prevent this. In this way, sensors for measurement of surface boundaries would not be necessary. Note that in the case of assessing potential collisions with objects of unknown prior geometry, such as operating room staff and/or equipment moving about the room, the use of surface geometry measurement sensors is desired.

Figure 3:
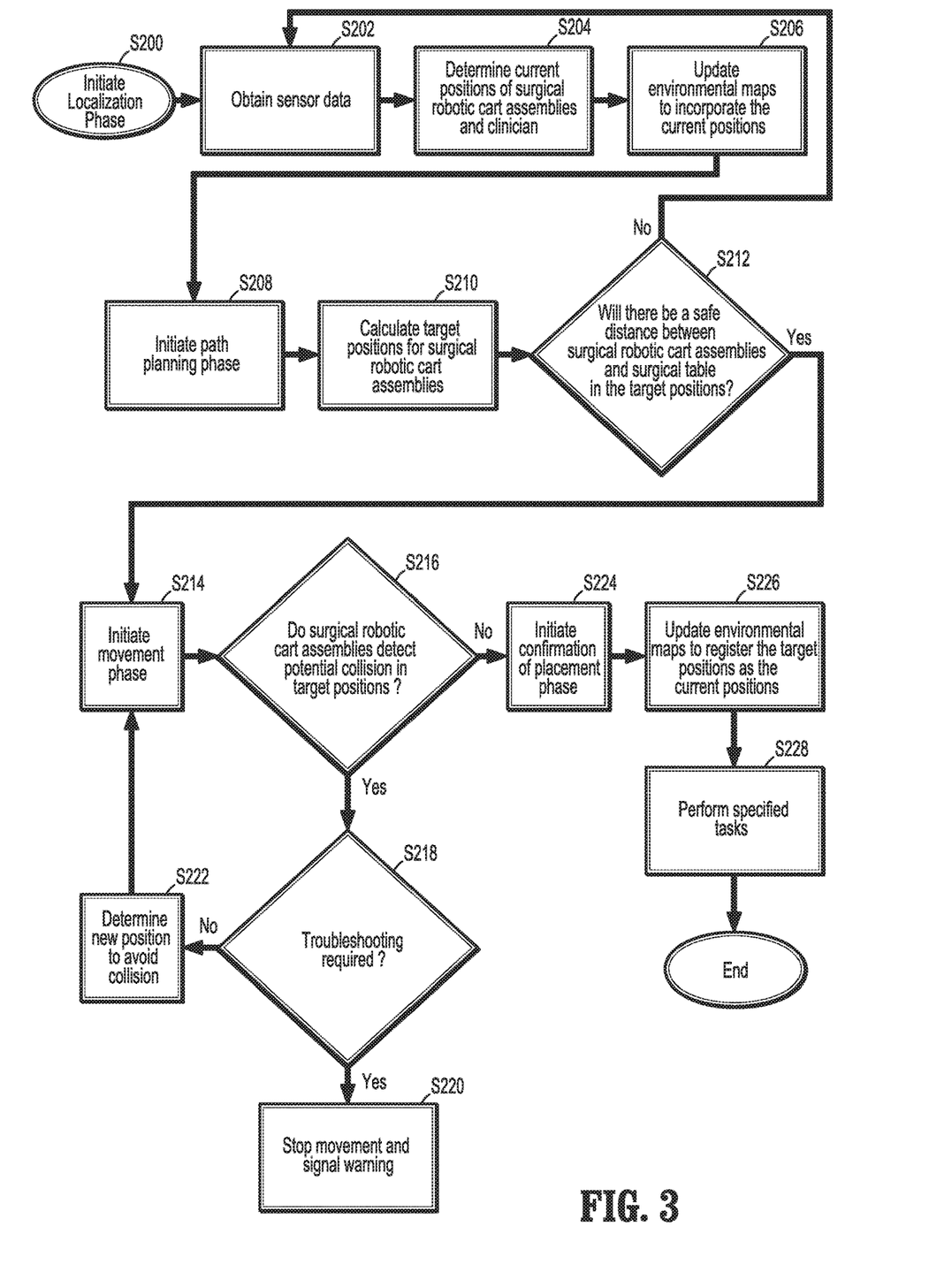
FIG. 3 is a flow chart illustrating a method of positioning the surgical robotic cart assembly of FIG. 2 in accordance with the present disclosure.

Turning first to FIGS. 3 and 4, in step S200, the localization phase is initiated. Following the initiation of the localization phase, in step S202, sensor data is obtained to determine a current position "PA1" of first surgical robotic cart assembly 100a relative to second surgical robotic cart assembly 100b and surgical table "ST" and a current position "PB1" of second surgical robotic cart assembly 100b relative to first surgical robotic cart assembly 100a and surgical table "ST" in step S204. In embodiments, sensor data is obtained from visual sensor 14a and floor sensor 14b of operating room "OR." Alternatively/additionally, current positions "PA1" and "PA2" of first and second surgical robotic cart assemblies 100a, 100b, respectively, may be determined by sending and receiving signals between first and second surgical robotic cart assemblies 100a, 100b and surgical table "ST."

In embodiments, if an operator or clinician "C" is located within operating room "OR," the clinician "C" may be provided with a tag 138 configured to transmit a signal corresponding to a current position "PC1" of clinician "C" relative to first and second surgical robotic cart assemblies 100a, 100b, and surgical table "ST." The current position "PC1" of clinician "C" may be determined by one or more of visual sensor 14a, floor sensor 14b, sensor(s) 16 of surgical table "ST," and/or camera 132 and sensor(s) 134 of each of first and second surgical robotic cart assemblies 100a, 100b.

Following the localization phase, in step S206, environmental maps 12a are updated by incorporating the current positions "PA1," "PB1," and "PC1" of first and second surgical robotic cart assemblies 100a, 100b and clinician "C," respectively, into the dynamic map portion 12a2, and incorporating or aligning the dynamic map portion 12a2 with the static map portion 12a1 to provide a representation of the current positions "PA1," "PB1," and "PC1" within the boundaries of operating room "OR."

Turning next to FIG. 5, in conjunction with FIG. 3, in step S208, the path planning phase is initiated by control device 4. In step S210, using at least the updated environmental maps 12a gathered during the localization phase and the patient data 12b, control device 4 calculates a second, target position "PA2" for first surgical robotic cart assembly 100a and a second, target position "PB2" for second surgical robotic cart assembly 100b to optimally position each robotic arm 3 (FIG. 2) relative to surgical table "ST." Step S210 includes plotting a path "X1" for first surgical robotic cart assembly 100a and a path "X2" for second surgical robotic cart assembly 100b which avoids any obstructions en route to second positions "PA2" and "PB2" of first and second surgical robotic cart assemblies 100a, 100b, respectively.

In embodiments, as illustrated in FIG. 5, control device 4 calculates path "X1" of first surgical robotic cart assembly 100a to avoid a collision between first surgical robotic cart assembly 100a and surgical table "ST," and calculates path "X2" of second surgical robotic cart assembly 100b to avoid a collision between second surgical robotic cart assembly 100b and clinician "C."

Next in step S212, if control device 4 determines that there will be a safe distance "D1" between first and second surgical robotic cart assemblies 100a, 100b as well as a safe distance "D2" between each of first and second surgical robotic cart assemblies 100a, 100b and surgical table "ST" when first and second surgical robotic cart assemblies 100a, 100b are in second positions "PA2" and "PB2," respectively, control device 4 instructs first and second surgical robotic cart assemblies 100a, 100b to move towards the respective second positions "PA2" and "PB2."

However, if control device 4 determines that the distance between first and second surgical robotic cart assemblies 100a, 100b will be less than safe distance "D1" and/or the distance between each of first and second surgical robotic cart assemblies 100a, 100b and surgical table "ST" will be less than safe distance "D2," when first and second surgical robotic cart assemblies 100a, 100b are in second positions "PA2" and "PB2," respectively, robotic surgical system 1 is returned to step S202 to obtain further sensor data as described above.

With reference to FIGS. 3, 5, and 6, once the path planning phase is completed, the movement phase is initiated in step S214 during which first and second surgical robotic cart assemblies 100a, 100b move autonomously towards second positions "PA2" and "PB2," respectively, based on the instructions received from control device 4. It is contemplated that first and second surgical robotic cart assemblies 100a, 100b may be moved consecutively or simultaneously towards second positions "PA2" and "PB2," respectively. It is contemplated that first and second surgical robotic cart assemblies 100a, 100b may be provided with powered wheels and steering assemblies for automated movements thereof.

In step S216, as first and second surgical robotic cart assemblies 100a, 100b move towards second positions "PA2" and "PB2," respectively, sensor(s) 134 of each of first and second surgical robotic cart assemblies 100a, 100b are configured to continuously detect for signs of close-in contact potential, beyond prior detection of obstructions during the path planning phase as described above. Close-in contact potential can be computed using well established techniques from computer graphics and robotic navigation (e.g. see "FCL: A general purpose library for collision and proximity queries," Robotics and Automation (ICRA), 2012 IEEE International Conference on, DOI: 10.1109/ICRA.2012.6225337).

In step S216, with first and second surgical robotic cart assemblies 100a, 100b located in second positions "PA2" and "PB2," respectively, as shown in FIG. 6, if a potential contact distance "D3" between first and second surgical robotic cart assemblies 100a, 100b is detected by sensor(s) 134 of second surgical robotic cart assembly 100b, in step S218, second surgical robotic cart assembly 100b is configured to determine whether troubleshooting is required.

In step S220, if troubleshooting is required, second surgical robotic cart assembly 100b is configured to stop movement and broadcast a signal via transmitter 136 to clinician "C" in operating room "OR" and/or observers (not shown) outside of operating room "OR" indicating the potential for collision with first surgical robotic cart assembly 100a or surgical table "ST."

In step S222, if troubleshooting is not required, second surgical robotic cart assembly 100b is configured to signal via transmitter 136 to control device 4 indicating the potential for collision with first surgical robotic cart assembly 100a or surgical table "ST." Following the indication from second surgical robotic cart assembly 100b, control device 4 determines a third position "PB3" for second surgical robotic cart assembly 100b such that, second surgical robotic cart assembly 100b avoids collision with first surgical robotic cart assembly 100a or surgical table "ST." It is contemplated that third position "PB3" of second surgical robotic cart assembly 100b is calculated to enable second surgical robotic cart assembly 100b to continue performing its specified task while avoiding a collision with first surgical robotic cart assembly 100a and surgical table "ST."

Once third position "PB3" of second surgical robotic cart assembly 100b is determined, robotic surgical system 1 is returned to step S214 wherein the movement phase is initiated to move second surgical robotic cart assembly 100b to third position "PB3." Though not specifically illustrated in FIG. 6, it is contemplated that first surgical robotic cart assembly 100a is configured to operate similar to second surgical robotic cart assembly 100b in response to detecting the potential contact distance "D3" between first and second surgical robotic cart assemblies 100a, 100b.

Continuing with FIG. 3, alternatively, if the potential contact distance "D3" between first and second surgical robotic cart assemblies 100a, 100b is not detected by sensor (s) 134 of second surgical robotic cart assembly 100b following step S216, in step S224, the confirmation of placement phase in initiated. Once control device 4 determines that first and second surgical robotic cart assemblies 100a, 100b are in the respective specified positions (e.g., positions "PA2" and "PB2" or "PB3"), in step S226, environmental maps 12a are updated similar to the process in step S204. Specifically, the dynamic map portion 12a2 of environmental maps 12a is updated to register positions "PA2" and "PB2"/"PB3" of first and second surgical robotic cart assemblies 100a, 100b, respectively, as the respective current positions thereof. Next, the updated dynamic map portion 12a2 of environmental maps 12a is again incorporated or aligned with the static map portion 12a1 of environmental maps 12a to provide a representation of the current positions "PA2" and "PB2"/"PB3 within the boundaries of operating room "OR."

Following the confirmation of placement phase, in step S228, first and second surgical robotic cart assemblies 100a, 100b are configured to perform the respective specified tasks (e.g., medical procedure). It is contemplated that further adjustments may be made to the positions of first and second surgical robotic cart assemblies 100a, 100b as described in the method steps above with reference to FIGS. 3-6.

Figure 7:
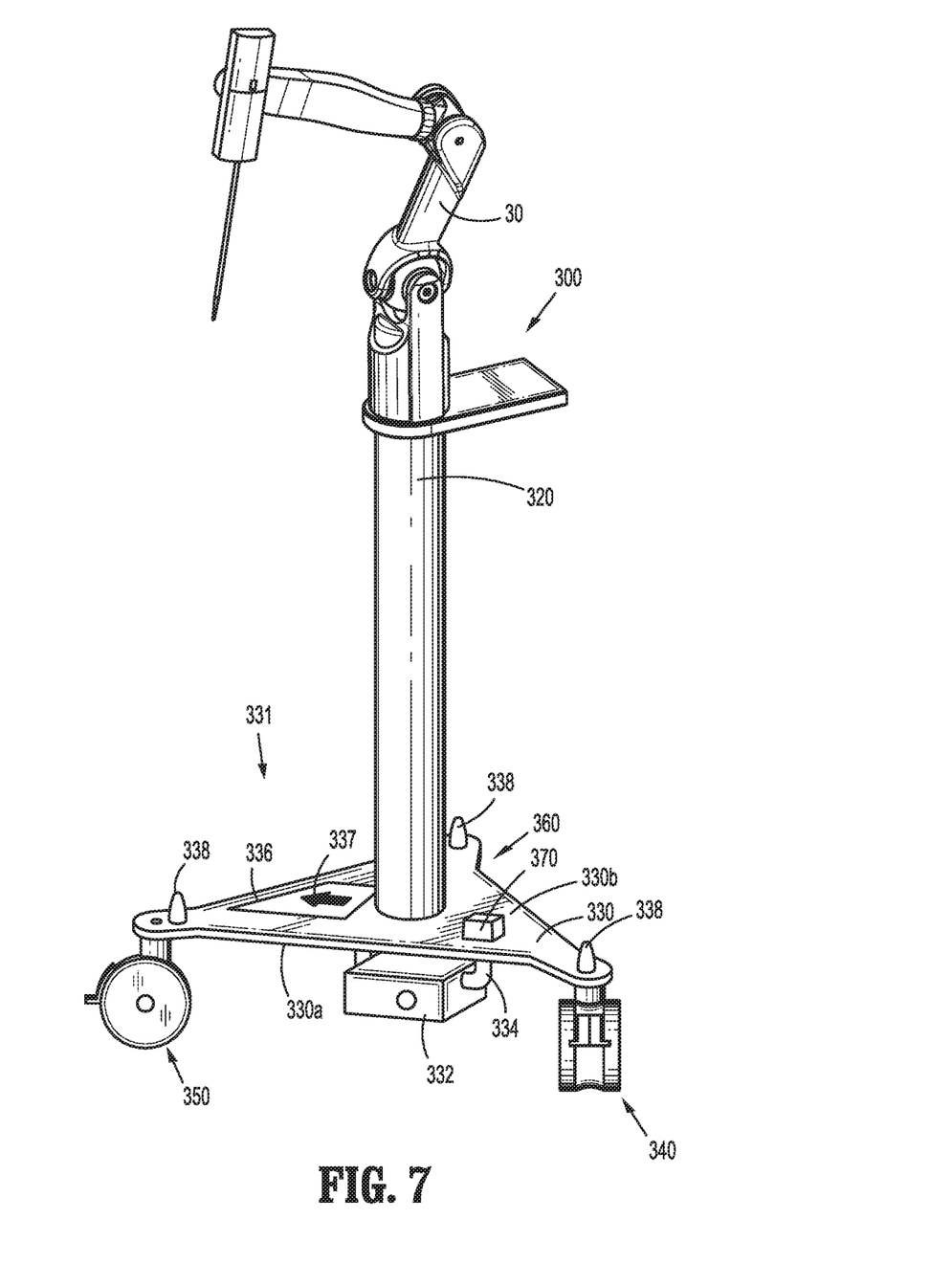
FIG. 7 is a perspective view of a surgical robotic cart assembly of the robotic surgical system of FIG. 1, illustrating a robotic arm supported on a base portion in accordance with another embodiment the present disclosure.

Turning now to FIG. 7, a surgical robotic cart assembly 300 provided in accordance with another aspect of the present disclosure is shown. Similar to surgical robotic cart assembly 100, surgical robotic cart assembly 300 generally includes a robotic arm 30, a vertical column 320, and a base portion 330. Base portion 330 includes a plurality of casters 340, 350, and 360 coupled thereto.

Base portion 330 also includes a visual guidance system 331 and an on-board safety system 370. Visual guidance system 331 is configured to direct clinician "C" as to where surgical robotic cart assembly 300 needs to be manually moved. In embodiments, visual guidance system 331 includes a projector 332 mounted on a gimbal 334 supported on a bottom or floor-facing surface 330a of base portion 330. In embodiments, visual guidance system 331 also includes a display 336 and one or more light(s) 338 mounted on a top surface 330b thereof. Light(s) 338 may be spaced apart and disposed about the periphery of base portion 330.

Figure 8:
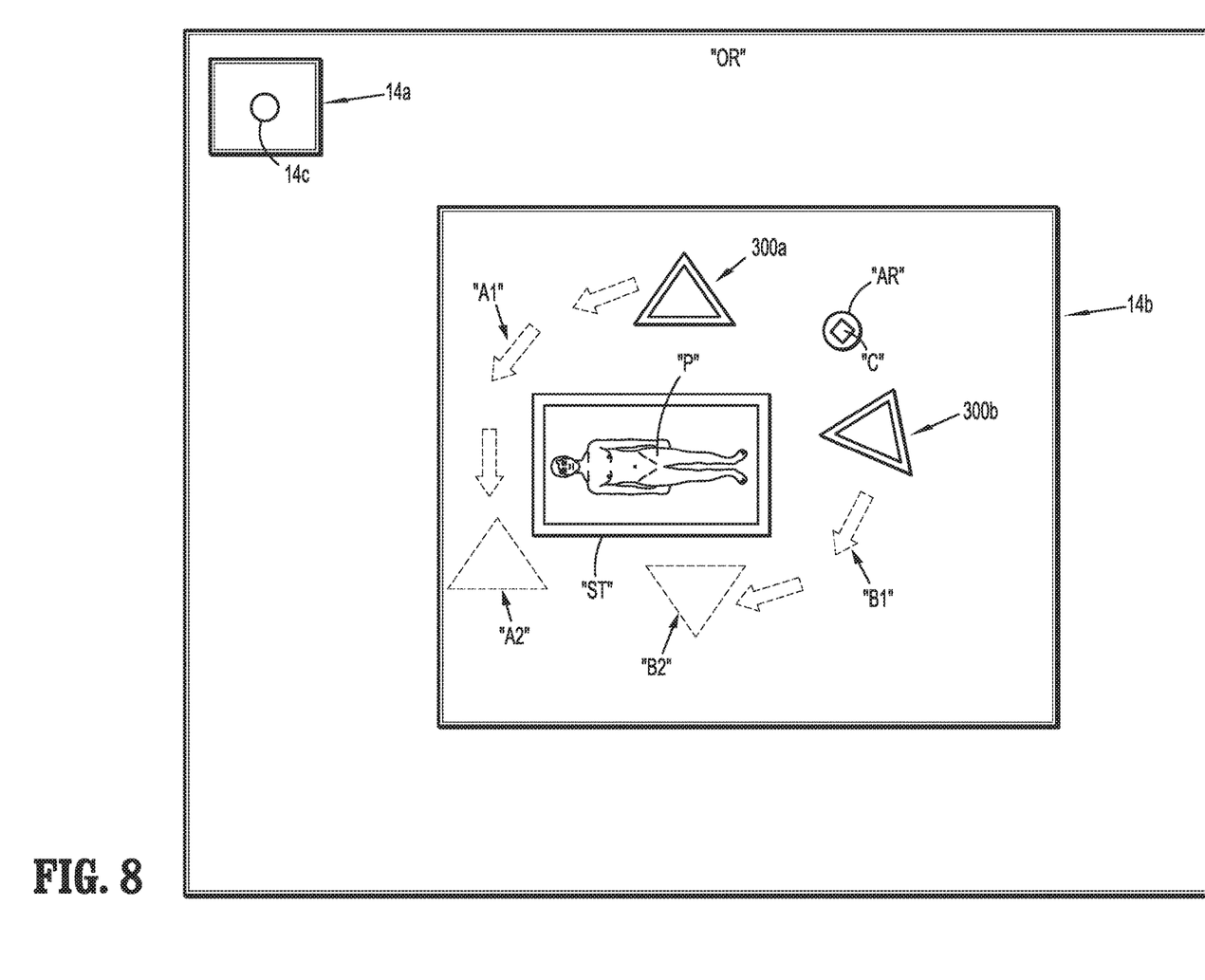
FIG. 8 is a top, plan view of the operating room of the robotic surgical system of FIG. 1, illustrating a plurality of surgical robotic cart assemblies in accordance with another embodiment the present disclosure.

With additional reference to FIG. 8, in conjunction with FIG. 7, manual positioning means of a first surgical robotic cart assembly 300a and a second surgical robotic cart assembly 300b around surgical table "ST" is described. Similar to the automated positioning means described above with reference to FIGS. 2-6, the manual positioning means is configured to facilitate optimal positioning of robotic arm 30 of each of first and second surgical robotic cart assemblies 300a, 300b relative to each other and surgical table "ST" to complete a specified task.

In embodiments, projector 332 of each first and second surgical robotic cart assemblies 300a, 300b is configured to emit or project a pattern "A1" and "B1," respectively, onto the floor of the operating room "OR" which directs clinician "C" to move first and second surgical robotic cart assemblies 300a, 300b towards a target location "A2" and "B2," respectively. In embodiments, visual sensor 14a mounted to the ceiling of operating room "OR" may include a projector 14c configured to simultaneously project patterns "A1" and "B1," and target locations "A2" and "B2" for first and second surgical robotic cart assemblies 300a, 300b, respectively. Alternatively, projector 14c may instead be disposed within the operating room lights (not shown) above surgical table "ST." It is contemplated that as clinician "C" moves first and second surgical robotic cart assemblies 300a, 300b towards target locations "A2" and "B2," respectively, patterns "A1" and "B1" are configured to change to provide updated directions until exact placement of first and second surgical robotic cart assemblies 300a, 300b is achieved. Upon reaching respective target locations "A2" and "B2," first and second surgical robotic cart assemblies 300a, 300b are configured to provide audible and/or visible indication that target locations "A2" and "B2" have been reached.

In embodiments, display 336 on base portion 330 is configured to display a visual indication 337 of the direction to move first and second surgical robotic cart assemblies 300a, 300b. Visual indication 337 of display 336 may include geometric indicia such as, for example, an arrow scaled according to the distance first and second surgical robotic cart assemblies 300a, 300b need to move in order to reach target locations "A2" and "B2," respectively. In embodiments, visual indication 337 of display 336 may include numeric indicia of the remaining distance to target locations "A2" and "B2," respectively. Display 336 is configured to continuously update the visual indication 337 until target locations "A2" and "B2" have been reached. In embodiments, light(s) 338 disposed about the periphery of base portion 330, may be configured to selectively illuminate to provide indication to move first and second surgical robotic cart assemblies 300a, 300b in a certain direction.

Further, as shown in FIG. 8, clinician "C" may be provided with an augmented reality display device "AR" configured to provide an enhanced view of the operating room "OR" including visual indication of where first and second surgical robotic cart assemblies 300a, 300b need to be moved as well as dynamically updating paths to reach target locations "A2" and "B2," respectively. Augmented reality display device "AR" may also be configured to provide indication of speed and the need to slow movement of first and second surgical robotic cart assemblies 300a, 300b in order to avoid collisions.

Safety system 370 is configured to operate in conjunction with visual guidance system 331 to prevent collisions between one or more of first and second surgical robotic cart assemblies 300a, 300b and surgical table "ST" as first and second surgical robotic cart assemblies 300a, 300b are moved by clinician "C." In embodiments, safety system 370 is configured to selectively trigger a locking mechanism to apply brakes to one or more of the plurality of casters 340, 350, and 360 of base portion 330. Safety system 370 is also configured to communicate with control device 4 (FIG. 1) in instances where first and second surgical robotic cart assemblies 300a, 300b require troubleshooting.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:

1. A method of placing a surgical robotic cart assembly, comprising:
   determining a first position of a first surgical robotic cart assembly relative to a surgical table;
   determining a first position of a second surgical robotic cart assembly relative to the first surgical robotic cart assembly and the surgical table;
   retrieving an environmental map including a static map portion including boundaries of an operating room and at least one landmark and a dynamic map portion including positions of the first and second surgical robotic carts;
   updating the dynamic map portion to incorporate the first position of the first surgical robotic cart assembly and the first position of the second surgical robotic cart assembly;
   calculating a path for the first surgical robotic cart assembly towards a second position of the first surgical robotic cart assembly relative to the surgical table, wherein in the second position, the first surgical robotic cart assembly is spaced-apart a first safe distance from the surgical table;
   calculating a path for the second surgical robotic cart assembly towards a second position of the second surgical robotic cart assembly relative to the first surgical robotic cart assembly and the surgical table, wherein in the second position, the second surgical robotic cart assembly is spaced-apart a second safe distance from the first surgical robotic cart assembly and a third safe distance from the surgical table;
   moving the first surgical robotic cart assembly autonomously towards the second position thereof;
   moving the second surgical robotic cart assembly autonomously towards the second position thereof;
   updating the dynamic map portion during movement of the first surgical robotic cart assembly and the second surgical robotic cart assembly;
   predicting a potential collision along the path of the first surgical robotic cart assembly as the first surgical robotic cart assembly moves towards the second position thereof; and
   predicting a potential collision along the path of the second surgical robotic cart assembly as the second surgical robotic cart assembly moves towards the second position thereof.

2. The method according to claim 1, further comprising:
   obtaining a first sensor data from a visual sensor to determine the first position of the first surgical robotic cart assembly and to determine the first position of the second surgical robotic cart assembly.

3. The method according to claim 1, further comprising:
   obtaining a second sensor data from a floor sensor to determine the first position of the first surgical robotic cart assembly and to determine the first position of the first surgical robotic cart assembly.

4. The method according to claim 1, further comprising:
   obtaining a third sensor data from the first surgical robotic cart assembly to determine the first position of the second surgical robotic cart assembly.

5. The method according to claim 1, further comprising:
obtaining a fourth sensor data from the surgical table to determine the first position of the first surgical robotic cart assembly.

6. The method according to claim 1, further comprising: updating an environmental map to incorporate the first position of the first surgical robotic cart assembly and the first position of the second surgical robotic cart assembly.

7. The method according to claim 1, further comprising: determining a third position for the second surgical robotic cart assembly upon detecting the potential collision between the second surgical robotic cart assembly and the first surgical robotic cart assembly.

8. The method according to claim 1, further comprising: determining whether the second surgical robotic cart assembly needs troubleshooting upon detecting the potential collision between the second surgical robotic cart assembly and the first surgical robotic cart assembly.

9. The method according to claim 1, further comprising: moving the first surgical robotic cart assembly and the second surgical robotic cart assembly simultaneously towards the respective second positions thereof.

10. The method according to claim 1, further comprising: determining a first position of a clinician relative to the first surgical robotic cart assembly, the second surgical robotic cart assembly, and the surgical table.

11. A method of positioning a plurality of surgical robotic cart assemblies within an operating room, comprising:
obtaining a first sensor data from an operating room sensor;
determining a first position of a first surgical robotic cart assembly and determining a first position of a second surgical robotic cart assembly, the first surgical robotic cart assembly including a first base portion having a first sensor and a first transmitter, and the second surgical robotic cart assembly including a second base portion having a second sensor and a second transmitter;
calculating a first path for the first surgical robotic cart assembly towards a second position of the first surgical robotic cart assembly and calculating a second path for the second surgical robotic cart assembly towards a second position of the second surgical robotic cart assembly;
moving the first surgical robotic cart assembly and the second surgical robotic cart assembly autonomously towards the second positions, respectively, thereof;
predicting a potential collision along the first path and the second path as the first surgical robotic cart assembly moves towards the second position thereof and as the second surgical robotic cart assembly moves towards the second position thereof; and
updating an environmental map with the second position of the first surgical robotic cart assembly and with the second position of the second surgical robotic cart assembly upon moving the first and second surgical robotic cart assemblies to the second positions, respectively, thereof.

12. The method according to claim 11, further comprising:
determining the first position of the first surgical robotic cart assembly and determining the first position of the second surgical robotic cart assembly from the first sensor data obtained from the operating room sensor.

13. The method according to claim 11, further comprising:
obtaining a second sensor data from the first sensor of the first surgical robotic cart assembly to determine the first position of the second surgical robotic cart assembly.

14. The method according to claim 11, further comprising:
obtaining a third sensor data from the second sensor of the second surgical robotic cart assembly to determine the first position of the first surgical robotic cart assembly.

15. The method according to claim 11, further comprising:
calculating the second position of the first surgical robotic cart assembly and calculating the second position of the second surgical robotic cart assembly to maintain a first safe distance between the first and second surgical robotic cart assemblies and to maintain a second safe distance between the first and second surgical robotic cart assemblies and a surgical table.

16. The method according to claim 15, further comprising:
moving the second surgical robotic cart assembly autonomously to a third position thereof when a distance between the first and second surgical robotic cart assemblies is less than the first safe distance.

17. The method according to claim 16, further comprising:
updating the environmental map to register the third position of the second surgical robotic cart assembly as a current position of the second surgical robotic cart assembly when the second surgical robotic cart assembly is moved to the third position thereof.

18. A surgical robotic cart assembly, comprising:
a robotic arm; and
a base portion configured to operatively support the robotic arm thereon, the base portion including a visual guidance system having:
a projector mounted on the base portion, the projector configured to project a pattern corresponding to a movement direction towards a target location, wherein the pattern projected by the projector is configured to change as the base portion is moved along the pattern towards the target location;
a display mounted on the base portion, the display configured to represent a visual indication corresponding to the movement direction towards the target location; and
a plurality of lights mounted on the base portion and spaced apart thereon, at least one of the plurality of lights configured to selectively illuminate corresponding to the movement direction towards the target location.

* * * * *